United States Patent [19]
Cooper et al.

[11] Patent Number: 5,545,787
[45] Date of Patent: Aug. 13, 1996

[54] PROCESS FOR DEHYDROGENATING HYDROCARBONS AND OXYGENATED HYDROCARBONS

[75] Inventors: Jeremy B. Cooper, West Sussex; Jonathon C. Frost, Surrey; Stephen R. Partington, Walton-on-Thames, all of United Kingdom

[73] Assignee: BP Chemicals Limited, London, England

[21] Appl. No.: 252,051

[22] Filed: May 31, 1994

Related U.S. Application Data

[63] Continuation of Ser. No. 979,511, Nov. 20, 1992, abandoned.

[30] Foreign Application Priority Data

Nov. 21, 1991 [GB] United Kingdom ............... 9124874
Sep. 4, 1992 [GB] United Kingdom ............... 9218821

[51] Int. Cl.[6] ............................................. C07C 5/333
[52] U.S. Cl. .................. 585/444; 585/445; 585/629; 585/630
[58] Field of Search ................... 585/444, 445, 585/629, 630

[56] References Cited

U.S. PATENT DOCUMENTS

| | | |
|---|---|---|
| 3,679,773 | 7/1972 | Kovach et al. |
| 3,894,110 | 7/1975 | Drehman ............... 585/629 |
| 4,327,238 | 4/1982 | Eastman ............... 585/629 |
| 4,675,465 | 6/1987 | Fanelli et al. ............ 585/654 |
| 4,769,509 | 9/1988 | Josefowicz ............. 585/629 |

FOREIGN PATENT DOCUMENTS

| | | |
|---|---|---|
| 554765 | 3/1958 | Canada ............ 585/629 |
| 892647 | 5/1944 | France. |
| 985606 | 7/1951 | France. |
| 2609982 | 7/1988 | France. |
| 1064496 | 9/1959 | Germany. |

OTHER PUBLICATIONS

Chem. Abstract 114:130165r "High Resolution Electron Microscopy of Ceria–Supported Catalysts" Jan. 3, 1990.
Carberry "Chemical and Catalytic Reaction Engineering" (1976) McGraw–Hill, pp. 362–365, 394–397, 434–437.
Cochrane et al "High resolution electron microscopy of ceria–supported catalysts", Ultramicroscopy, vol. 34 (1990) pp. 10–16 (North–Hollend).

Primary Examiner—Asok Pal
Attorney, Agent, or Firm—Nixon & Vanderhye

[57] ABSTRACT

A continuous process for the dehydrogenation of a hydrocarbon and/or oxygenated hydrocarbon feed, comprising contacting the hydrocarbon and/or oxygenated hydrocarbon feed with a dehydrogenation catalyst at elevated temperature in a reaction zone characterized in that the catalyst is capable of retaining hydrogen and (a) is contacted with a feed to form a dehydrogenated product and hydrogen, at least some of the hydrogen formed being adsorbed by the catalyst and/or reacting therewith to reduce at least part of the catalyst; (b) the dehydrogenated product and any unadsorbed/unreacted hydrogen is removed from the reaction zone; (c) at least some of the adsorbed hydrogen is removed from the catalyst and/or at least some of the reduced catalyst is oxidized; and (d) reusing the catalyst from step (c) in step (a).

7 Claims, 1 Drawing Sheet

PROCESS FOR DEHYDROGENATING HYDROCARBONS AND OXYGENATED HYDROCARBONS

This is a continuation of application Ser. No. 07/979,511, filed Nov. 20, 1992, now abandoned.

BACKGROUND OF THE INVENTION

The present invention relates to a process for the dehydrogenation of hydrocarbons and/or oxygenated hydrocarbons.

Dehydrogenation processes, and in particular the dehydrogenation of alkanes, are well known. The process generally employs a dehydrogenation catalyst which is contacted by the feedstock to produce the dehydrogenated product and hydrogen. The hydrogen may then be separated from the product stream to provide the desired product.

It would be desirable to develop a process having little or no external heat input for the dehydrogenation reaction, with or without separation into its individual components, to obtain high conversion values without the co-production of undesirable by-products and avoiding the extensive separation plant associated with cracking.

SUMMARY OF THE INVENTION

Progress has been made in this direction by the process of the present invention and accordingly, the present invention provides a continuous process for the dehydrogenation of a hydrocarbon and/or an oxygenated hydrocarbon feed, which process comprises contacting the hydrocarbon and/or oxygenated hydrocarbon feed with a dehydrogenation catalyst at elevated temperature in a reaction zone characterised in that the catalyst is capable of retaining hydrogen and (a) is contacted with the feed to form a dehydrogenated product and hydrogen, at least some of the hydrogen formed being adsorbed by the catalyst and/or reacting therewith to reduce at least part of said catalyst;

(b) the dehydrogenated product and any unadsorbed/unreacted hydrogen is removed from the reaction zone;

(c) at least some of the adsorbed hydrogen is removed from the catalyst and/or at least some of the reduced catalyst is oxidised; and (d) reusing the catalyst from step (c) in step (a).

The process of the present invention can provide a method for the dehydrogenation of hydrocarbons or oxygenated hydrocarbons without the need for an external heat supply. High conversion rates can be obtained without the co-production of undesirable by-products. Furthermore, the cyclic nature of the process avoids the simultaneous presence of free oxygen and hydrocarbon or oxygenated hydrocarbon in the reactor minimising loss of selectivity through carbon oxide formation as experienced in other oxidative dehydrogenation processes.

The process of the present invention is particularly suitable for the dehydrogenation of an alkane feed to the corresponding alkene. Suitably, the feed may comprise $C_2$ to $C_{20}$ alkanes. Suitably, the alkane feed may comprise alkanes, optionally with one or more aryl groups. Preferably, the alkane feed is $C_2$, $C_3$ or $C_4$ alkanes, especially $C_2$ alkanes. Alternatively, the hydrocarbon feed may comprise oxygenated hydrocarbons. Suitably, the oxygenated hydrocarbons are alcohols, e.g. aliphatic alcohols of $C_2$ to $C_{20}$ carbons. Preferably the alcohol is a $C_2$ to $C_{10}$ alcohol such as methanol, ethanol and isopropanol.

The process may be operated at a conversion and selectivity sufficiently high so as to avoid distillative purification, thereby economising on plant and operating costs. Where the feed comprises alkanes, the process may also be operated at a temperature sufficient to promote cracking, for example, for the co-production of mixtures of ethene, propene and butene from mixtures of ethane, propane, butane or higher hydrocarbons. In this event, if individual alkenes are required, distillative separation and purification of the mixed alkene product would be necessary.

The feed is contacted with a dehydrogenation catalyst to produce the dehydrogenated product and hydrogen. The dehydrogenation catalyst must either be capable itself of adsorbing the hydrogen or be combined with a hydrogen retention agent. The dehydrogenation catalyst per se or in combination with a hydrogen retention agent must be capable of retaining hydrogen released in the dehydrogenation process. Preferably, substantially all of the hydrogen is reacted with or adsorbed by the catalyst. The hydrogen may be retained chemically or physically or by a combination of both. The catalyst should have preferably a greater affinity for hydrogen than for oxygen or water, otherwise these could be preferentially retained, if oxygen is used in step (c) of the present process. A suitable catalyst, for example, may be one that retains oxygen and converts hydrogen to water at a selectivity sufficient to prevent gross product contamination with acid and carbon oxides.

Catalysts suitable for use in the process and capable of adsorbing hydrogen include reducible metal oxides, optionally with a metal selected from Group IB, IIB, and Group VIII of the periodic table. Suitably, rare earth metal oxides, optionally with a metal selected from the group including nickel, palladium, platinum, copper, silver and gold may be employed in the process of the present invention. The preferred metal is one which has little methanation activity, for example, gold. The catalysts may contain 1–30% such as 10–25% of said metal, especially gold (expressed by weight as metal, irrespective of whether it is present as metal and/or metal oxide); the catalysts preferably consist essentially of the said metal and/or metal oxide, and said rare earth metal oxide. They may be made by impregnation of said rare earth metal oxide by a solution of a thermally decomposable salt of said metal, or preferably by co-precipitation by contact of base, e.g. ammonium bicarbonate, with a solution of salts of the metal and rare earth metal, preferably by addition of said solution to said base. The preferred catalyst is gold/ceria. The aforementioned catalysts may have sufficient hydrogen retention ability not to require a separate hydrogen retention agent, although one may be used if desired.

Catalysts incapable of adsorbing the hydrogen may also be used when combined with a hydrogen retention agent. Suitable catalysts include non-reducible metal oxides, with a metal selected from Group IB, IIB, IVB, VIA and VIII of the Periodic Table. Preferably, the catalysts may be platinum/zinc on silicalite, platinum/tin on alumina or chromium oxide on alumina. Suitable hydrogen retention agents may be selected from Group VIA metal oxides and rare earth metal oxides, especially molybdenum oxide, tungsten oxide and ceria. Optionally, the oxide may comprise a second metal selected from the group comprising nickel, palladium, platinum, copper, silver and gold. Some of the aforementioned dehydrogenation catalysts capable of adsorbing hydrogen e.g. gold/ceria may be added to the non-reducible metal oxide, thus primarily acting as the hydrogen retention agent. Where it is desired to use a catalyst incapable of adsorbing hydrogen in combination with a hydrogen retention agent, the two components may be used in a mole ratio of suitably 100:1 to 1:10, preferably 20:1 to 1:5 catalyst to agent.

The feed is firstly contacted with the dehydrogenation catalyst to produce the dehydrogenated product and hydrogen. The hydrogen produced is adsorbed by the catalyst. Unadsorbed hydrogen is removed from the reaction chamber, but preferably the process is performed so that there is substantially no hydrogen with the dehydrogenated product leaving the chamber.

Where the hydrogen is adsorbed on to the catalyst, the adsorbed hydrogen must be removed from the catalyst. Suitably, this may be carried out by contacting the catalyst with a component which is capable of being reduced by hydrogen, thus liberating the dehydrogenation catalyst. Suitably, the catalyst may be contacted with an oxygen-containing gas. The oxygen-containing gas may be suitably air or a synthetic gaseous mixture either richer or poorer in molecular oxygen than air. Oxygen itself may also be employed. Alternatively, the hydrogen may be removed by the action of heat, applying a vacuum or through the action of a chemical reagent. Suitable chemicals include carbon monoxide and carbon dioxide. Where the hydrogen is reacted with the catalyst in step (a) of the process of the present invention, to form a reduced catalyst, the catalyst is then partly oxidised to regenerate the catalyst. Suitably, an oxygen-containing gas may be used for the oxidation step.

The overall reaction, for example, ethane and oxygen to ethene and water is exothermic giving an adiabatic temperature rise of about 1,000° C. in air. This heat may be removed by performing the dehydrogenation reaction adiabatically, employing the ethane feed and the component used to remove the hydrogen from the catalyst at ambient temperature. If desired, the feed gases may be pre-heated, suitably by partial flow reversal. Pre-heating may reduce physical stress on the catalyst, but may also reduce the rate of heat removal from the catalyst into the passing gas, necessitating a larger bed and increasing the total gas flow required per unit of heat generated i.e. per tonne of product produced.

Cycle times which may be used in the operation of the process of the invention depend upon factors such as bed dimensions and gas velocity. Over the chosen cycle time the heat capacity of a bed of solid can be high compared to the gas passing through it, such that there is a substantially constant temperature over the cycle. A bed of the dehydrogenation catalyst may be maintained at a uniform temperature by controlling the hydrogen adsorption capacity at each distance into the bed such that the cooling due to gas flow over the cycle balances the heat produced at that position in the catalyst bed at burn off. This method of temperature control/stabilisation is made possible by the cyclic nature of the process and avoids the need for an expensive reactor with a large heat transfer area as used for conventional fixed bed exothermic reactions. Typically, the first stage of the process which comprises feeding in the alkane may comprise from one tenth to a quarter the time involved in feeding in the component required to remove the hydrogen and/or oxidise the reduced catalyst.

The elevated temperature at which the dehydrogenation process of step (a) is operated may suitably be in the range from 150° to 1200° C., preferably 300°–700° C. A temperature of about 500° C. is preferred. The pressure may suitably be atmospheric, subatmospheric or elevated.

BRIEF DESCRIPTION OF THE DRAWING

An embodiment of the invention will now be described with reference to the FIG. 1 which takes the form of a process flow sheet and to Examples 1 and 2.

DETAILED DESCRIPTION OF THE INVENTION

Figure 1:
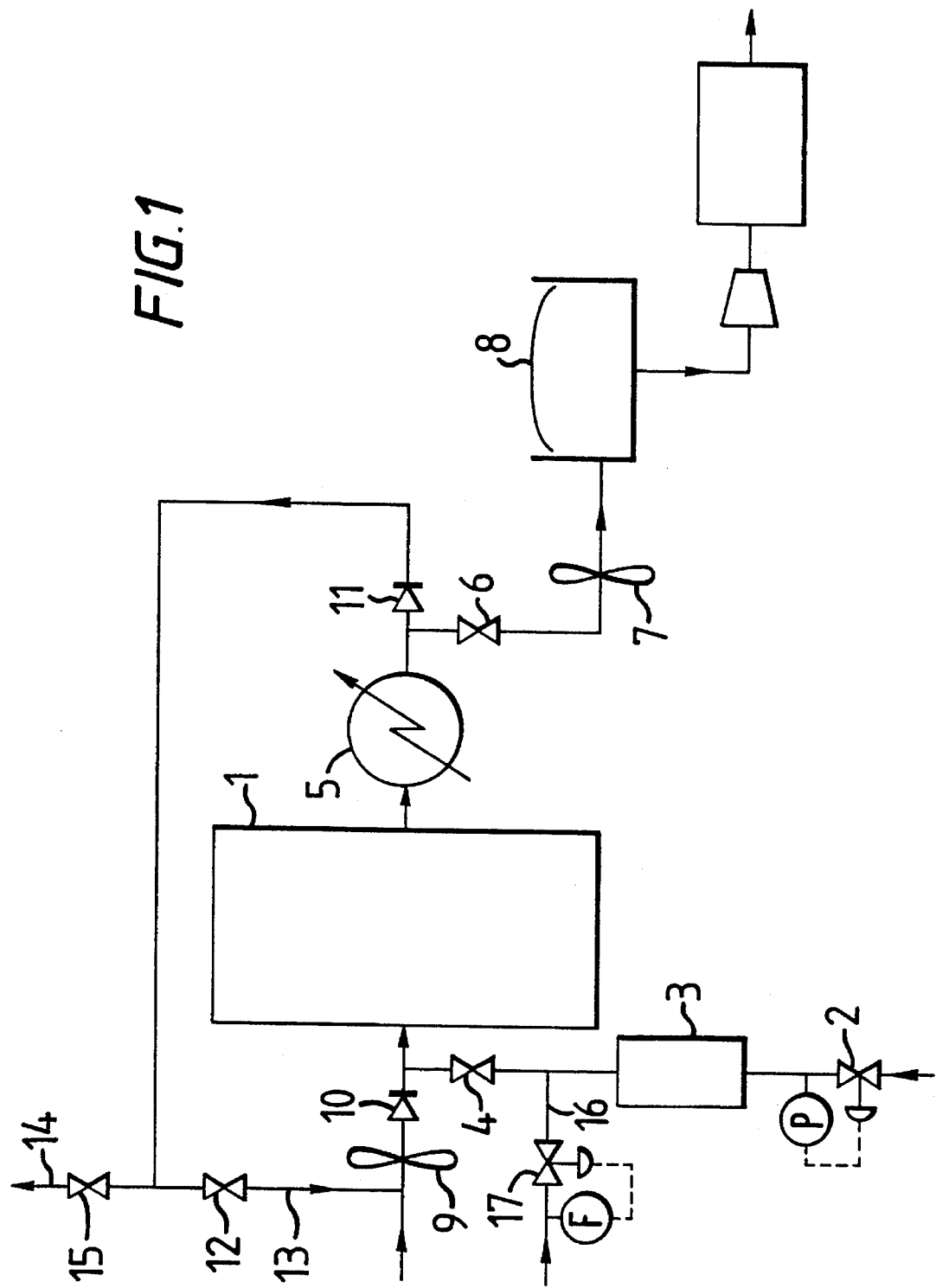

With reference to FIG. 1, to a reactor (1) is fed for 2 seconds cold ethane via a pressure control valve (2), a steam accumulator (3) and a timed valve (4). The reactor (1) contains a bed of dehydrogenation catalyst pellets, the catalyst being capable of adsorbing hydrogen. In contact with the catalyst, maintained at a temperature of about 500° C., ethane is dehydrogenated to ethylene, the hydrogen released thereby being retained by the catalyst. After two seconds the timer valve (4) closes cutting off the flow of ethane into the reactor.

Ethylene is removed from the reactor through the heat exchanger (5) and the time valve (6) by suction at slightly below atmospheric pressure by a blower (7) into a gasometer (8).

Air is then driven by a blower (9) through a non-return valve (10) into the reactor (1) for a period of 13 seconds, the timed valves (4) and (6) being closed. Combustion of the retained hydrogen and any carbon deposits on the catalyst and/or oxidation of the reduced catalyst occurs thereby generating heat to maintain the catalyst temperature. Combustion gas exits from the reactor through the heat exchanger (5) and a non-return device (11). A sufficient portion of the combustion gas is recycled to the reactor (1) via damper (12) and line (13) to the air feed in order to ensure that the oxygen concentration is below the flammable limit for safety reasons and that the inlet temperature of the gas into reactor (1) is warmed above the dew point; the remainder of the combustion gas leaves through line 14 via damper (15).

At the end of the 15 seconds cycle the timed valve (4) opens allowing a 'pig' of steam to be admitted to the reactor through line 16 from accumulator (3) where steam has been accumulating because of its continuous admission through valve (17). The 'pig' of steam serves to flush any remaining flue gases from the reactor and to separate the ethane and air.

The timed valves (4 and 6) are controlled by a timer (not shown). Adjustment of the timer is used to control the ethane feed per cycle to match the hydrogen adsorption capacity of the catalyst. Flow during the ethane phase is controlled to match or be less than bed activity. Too little feed per cycle could manifest itself in a distorted temperature profile through the catalyst bed, in particular high at the inlet. Too little catalyst activity could show as a distorted temperature profile and a high-residual ethane content in the gas leaving reactor (1).

Bed temperature can be controlled by adjusting the time period and velocity of the air feed. A longer admission time for air gives lower temperatures, particularly at the inlet. Higher air flow rates reduce the catalyst temperature, particularly at the outlet.

The foregoing description assumes an ethane pressure greater than blower discharge pressure and an ethylene pressure below atmospheric pressure, so that the non-return devices can function. Flow through the reactor during the ethane input would be slightly greater than during the air input phase because of the extra pressure drop.

The ability of catalyst to strongly adsorb hydrogen under low partial pressures of hydrogen and high temperatures was determined using a temperature programmed desorption technique (TPD). The catalysts were reduced in hydrogen at 400° C. and purged at this temperature in an inert gas for several hours before heating to 800° C. to desorb the retained hydrogen. The catalyst is suitably capable of adsorbing/reacting with at least 2 ml of hydrogen per gram of catalyst at 400° C. Metal-ceria catalysts were all observed to retain appreciable amounts of hydrogen at 400° C. (4 cm$^3$/g) whereas other metal oxide catalysts investigated, e.g. Ru/TiO$_2$, showed no detectable hydrogen retention capacity.

EXAMPLES

Example 1

Preparation of Gold/Ceria Catalyst

A solution of cerous nitrate hexahydrate (10 g) and hydrogen tetrachloroaurate (2 g) in 25 cm$^3$ of water was added dropwise with stirring to a saturated aqueous solution (800 cm$^3$) of ammonia bicarbonate. The resultant precipitate was separated by filtration and washed three times by redispersing in 500 cm$^3$ of water followed by filtering. The washed precipitate was then dried at 110° C. for 18 hours before crushing and sieving to give particles of 1 mm diameter. The catalyst particles were then heated under flowing air or an inert gas at a flow rate of 100 cm$^3$ per minute from room temperature to 500° C. at a heating rate of 2° C. per minute. The catalyst was then held at this temperature for 10 hours before being cooled to room temperature. The resulting catalyst was found to have 15% w/w gold and a surface area of 80 m$^2$ per gram. The prepared catalyst was tested for its hydrogen retention capability and showed to retain 4 cm$^3$/g of hydrogen at 400° C.

Example 2

Dehydrogenation of Ethane

The process as described above with reference to FIG. 1 was carried out at 500° C. in a 7 mm internal diameter quartz reactor at 1 barA, using 25% v/v ethane in helium at a flow rate of 40 cm$^3$/min (at STP) and the gold/ceria catalyst (4 g) prepared as disclosed in Example 1. The regeneration was carried out at the same temperature, pressure and flow rate using 5% oxygen in helium.

(i) Ethane Addition to a Regenerated Catalyst

Gas chromatographic and mass spectral analysis of the exit gas stream indicated a high conversion of ethane to ethene initially with no hydrogen being present. Water and some methane were also detected in the exit gas. The concentration of ethene reached a maximum, 5% v/v, before decreasing to approximately 1% v/v. 5% v/v is above the expected thermodynamic equilibrium value of 2% v/v. The conversion and selectivity calculated from the exit gas analysis gave a maximum in ethane conversion of approximately 28% with an ethene selectivity of 95%. The conversion was then found to fall to approximately 4% with a selectivity of 85% when hydrogen breakthrough into the exit gas occurred as the hydrogen adsorption capacity of the ceria became saturated. The thermodynamic equilibrium conversion under the conditions used for the experiments was approximately 8%.

An intermediate purge using helium rather than steam was used to separate the ethane and oxygen containing gases.

(ii) Regeneration

Gas chromatographic and mass spectral analysis of the exit gas showed a large quantity of carbon dioxide to be released from the catalyst bed prior to oxygen breakthrough into the exit gas. Some water was also observed.

The cumulative performance data calculated through a complete process cycle (starting at the regeneration stage) gives a cumulative ethane conversion of approximately 28% with a cumulative ethene selectivity of 20% at the maxima in ethene productivity.

We claim:

1. A process for the dehydrogenation of a hydrocarbon feed, which process comprises the steps of:

(a) contacting the feed at elevated temperature in a reaction zone with a catalyst system comprising a dehydrogenation catalyst incapable of retaining hydrogen and a hydrogen retention agent, said catalyst system being selected from the group consisting of gold/ceria, silver/ceria, palladium/ceria, ruthenium/ceria, platinum/ceria, cobalt/ceria, copper/ceria, zinc/ceria, iron/ceria and nickel/ceria, to form a dehydrogenated product and hydrogen, wherein at least some of the hydrogen formed is at least one of adsorbed by the catalyst or hydrogen retention agent or reacted with the catalyst or hydrogen retention agent to reduce at least part of said catalyst or hydrogen retention agent;

(b) removing from the reaction zone the dehydrogenated product and any hydrogen which is not at least one of adsorbed by or reacted with the catalyst system;

(c) regenerating the catalyst system by at least one of removing at least some of the adsorbed hydrogen from the catalyst or hydrogen retention agent or oxidizing at least some of the reduced catalyst or hydrogen retention agent; and (d) reusing the regenerated catalyst system from step (c) in step (a).

2. A process according to claim 1, wherein the hydrocarbon feed comprises one or more alkanes.

3. A process according to claim 2, wherein the alkane is a $C_2$, $C_3$ or $C_4$ alkane.

4. A process according to claim 1 in which the adsorbed hydrogen is removed from the dehydrogenation catalyst in step (c) by contacting the catalyst with an oxygen containing gas, thereby providing some or all of the heat to maintain the catalyst at the elevated temperature.

5. A process according to claim 1, in which the elevated temperature is 150° to 1200° C.

6. A process according to claim 1, wherein the catalyst system gold/ceria.

7. A process according to claim 1, wherein said hydrogen retention agent is capable of retaining at least two ml of hydrogen per gram of catalyst at 400° C.

* * * * *